(12) United States Patent
Eliasen et al.

(10) Patent No.: US 10,488,955 B2
(45) Date of Patent: Nov. 26, 2019

(54) MOUTH-HELD EXTENDABLE MOUTH STYLUS FOR ACTIVATING FUNCTIONS ON A TOUCH SCREEN OR KEYS

(71) Applicant: TUBUS TECHNOLOGY IVS, København Ø (DK)

(72) Inventors: Asbjørn Eliasen, Nørresundby (DK); Lizanne Svane, København Ø (DK)

(73) Assignee: TUBUS TECHNOLOGY IVS, København Ø (DK)

( * ) Notice: Subject to any disclaimer, the term of this patent is extended or adjusted under 35 U.S.C. 154(b) by 0 days.

(21) Appl. No.: 15/737,972

(22) PCT Filed: Jun. 20, 2016

(86) PCT No.: PCT/DK2016/050202
§ 371 (c)(1),
(2) Date: Dec. 19, 2017

(87) PCT Pub. No.: WO2016/202347
PCT Pub. Date: Dec. 22, 2016

(65) Prior Publication Data
US 2018/0299971 A1    Oct. 18, 2018

(30) Foreign Application Priority Data

Jun. 19, 2015 (DK) .................. 2015 00351
Sep. 18, 2015 (DK) .................. 2015 70596

(51) Int. Cl.
*G06F 3/039* (2013.01)
*A61F 4/00* (2006.01)
*G06F 3/044* (2006.01)
*G06F 3/0354* (2013.01)
*G06F 3/02* (2006.01)

(52) U.S. Cl.
CPC ............ *G06F 3/039* (2013.01); *A61F 4/00* (2013.01); *G06F 3/0219* (2013.01); *G06F 3/03545* (2013.01); *G06F 3/044* (2013.01)

(58) Field of Classification Search
CPC ...... A61F 4/00; G06F 3/0219; G06F 3/03545; G06F 3/039; G06F 3/044
See application file for complete search history.

(56) References Cited

U.S. PATENT DOCUMENTS

| 3,795,281 | A | * | 3/1974 | Cloran | ............ A61F 4/00 173/30 |
| 5,422,640 | A | * | 6/1995 | Haley | ............ A61F 4/00 340/4.11 |
| 5,860,754 | A | * | 1/1999 | Garland | ............ B43K 23/004 401/6 |
| 6,801,231 | B1 | * | 10/2004 | Beltz | ............ G06F 3/011 340/4.11 |

(Continued)

OTHER PUBLICATIONS

International Search Report and Written Opinion of the ISA for PCT/DK2016/050202, dated Sep. 16, 2016, 13 pages.

*Primary Examiner* — Viet D Pham
(74) *Attorney, Agent, or Firm* — Nixon & Vanderhye P.C.

(57) ABSTRACT

An extendable mouth stylus for activating functions on a touch screen or keys includes a piston housing having a first end part and a second end part, a piston having a piston rod with a first piston end and a second piston end, an activation part arranged at the second piston end of the piston, and a mouthpiece arranged at the one end of the piston housing.

19 Claims, 21 Drawing Sheets

(56) References Cited

U.S. PATENT DOCUMENTS

| | | | | |
|---|---|---|---|---|
| D662,098 S | * | 6/2012 | Leto | D14/411 |
| 2012/0044214 A1 | | 2/2012 | Mori | |
| 2013/0155013 A1 | * | 6/2013 | Chang | G06F 3/044 |
| | | | | 345/174 |
| 2014/0232701 A1 | | 8/2014 | Draper et al. | |
| 2014/0362057 A1 | * | 12/2014 | Hautson | B43K 24/02 |
| | | | | 345/179 |

\* cited by examiner

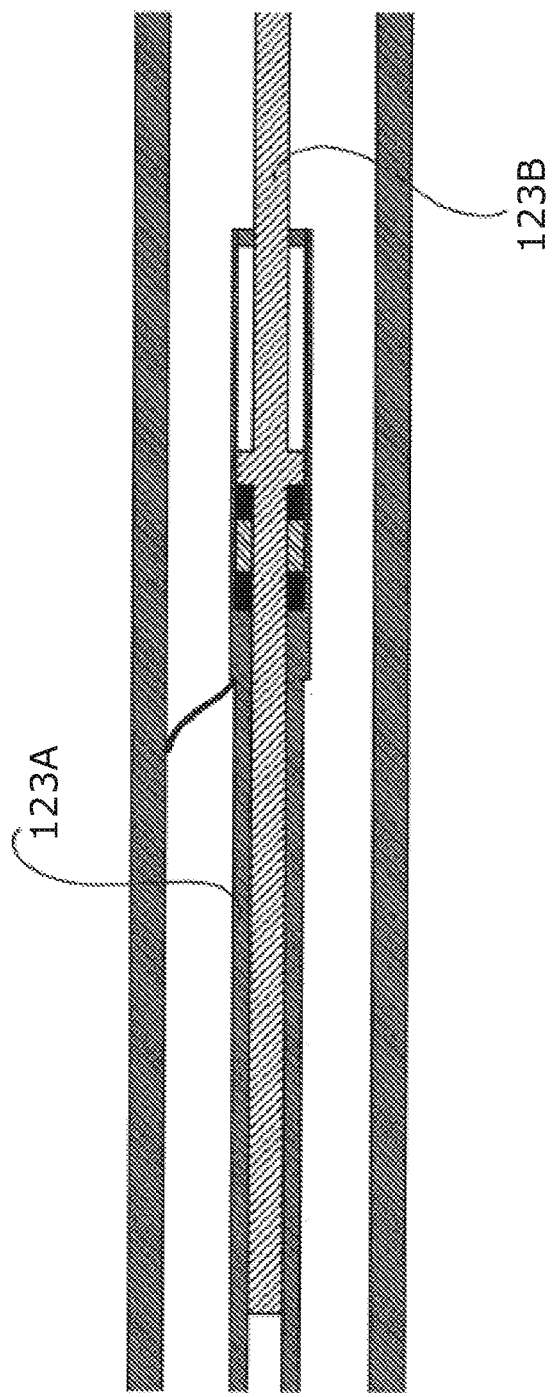

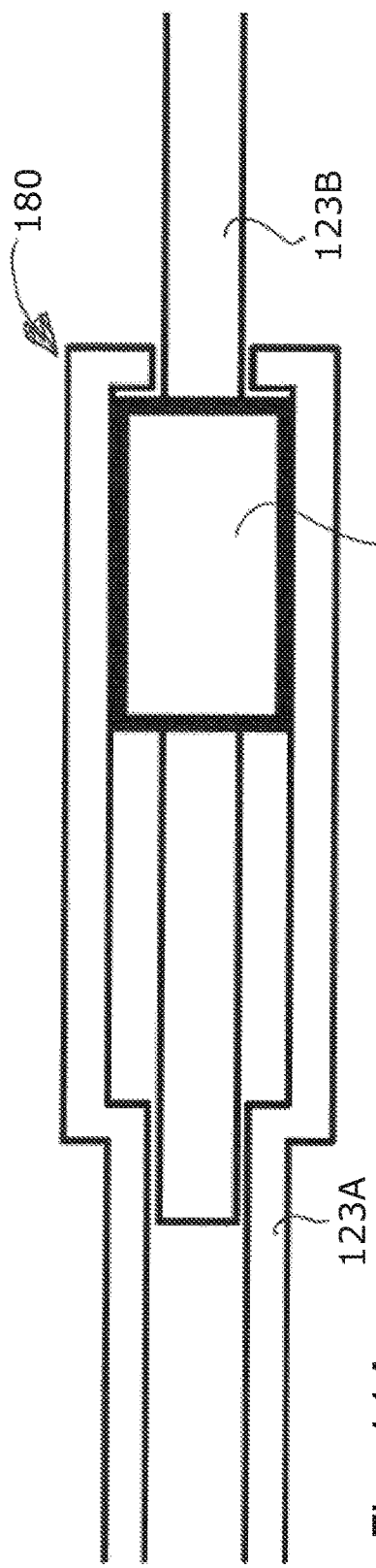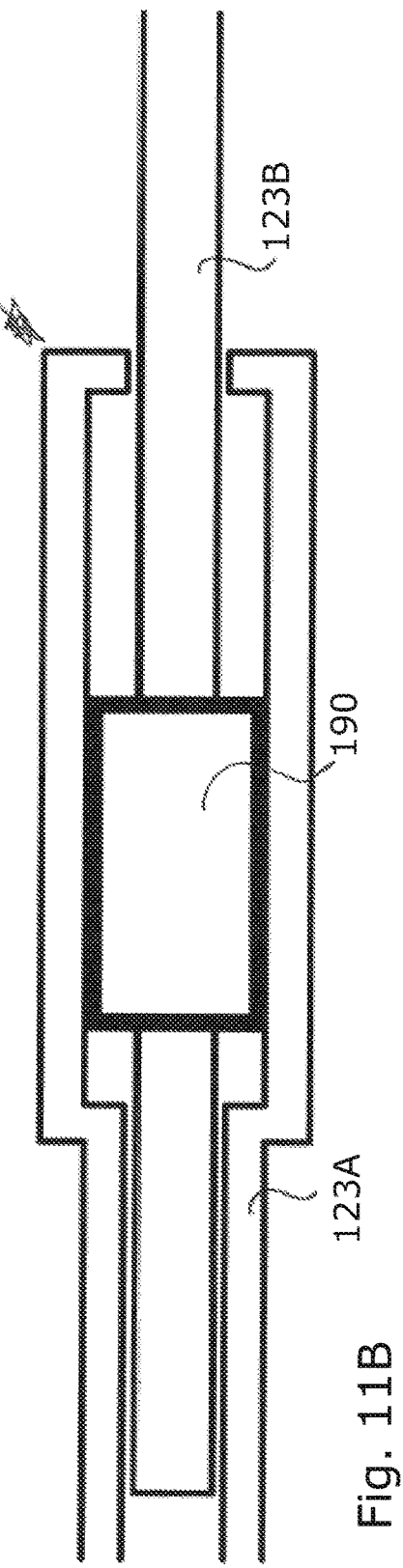

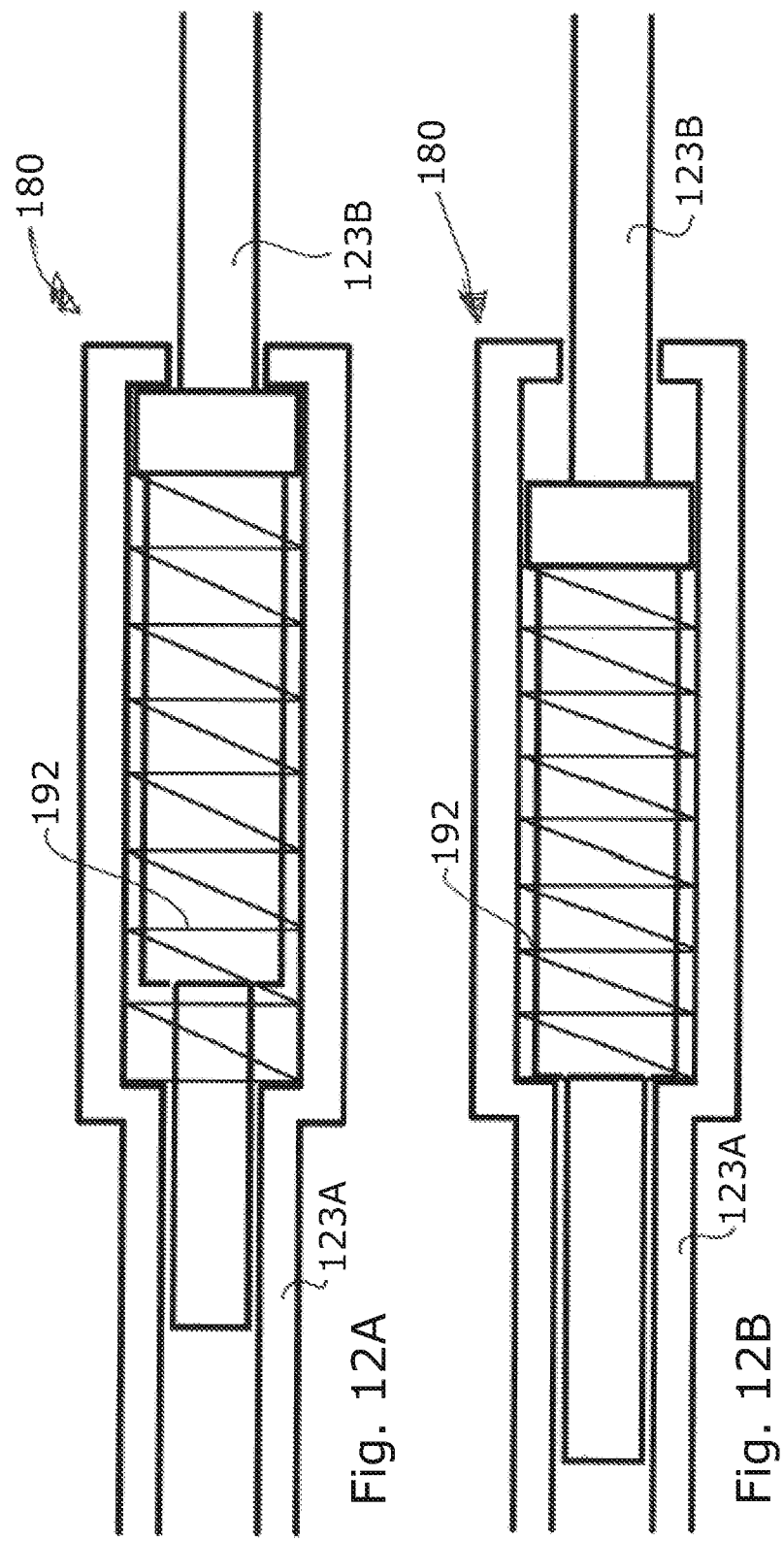

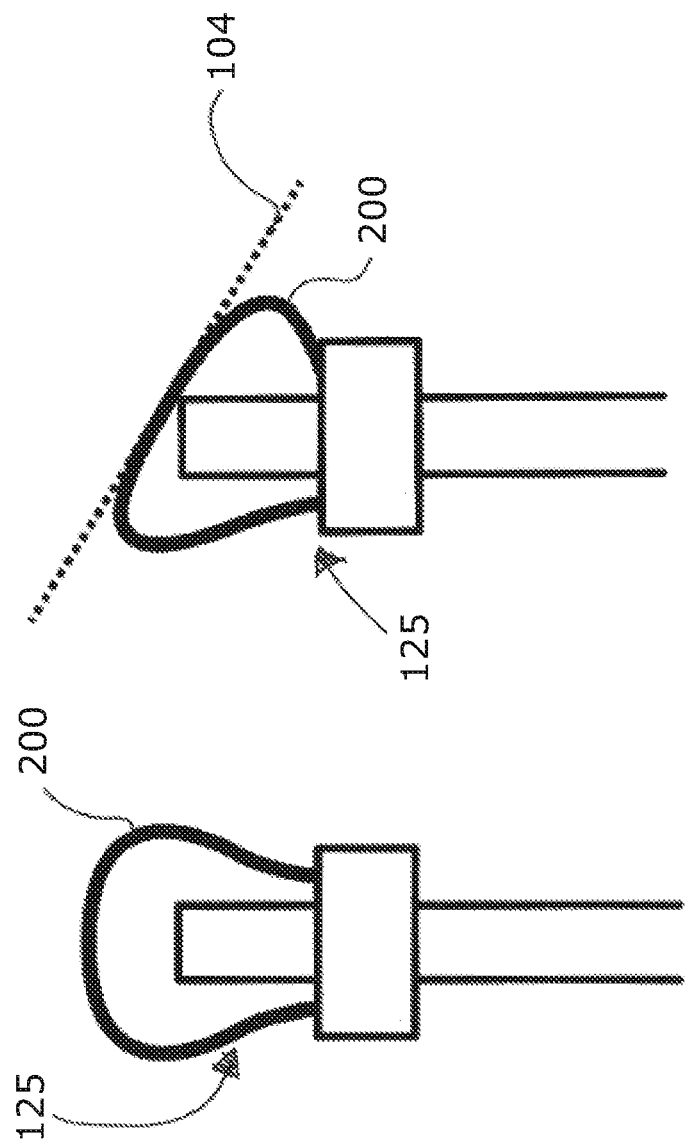

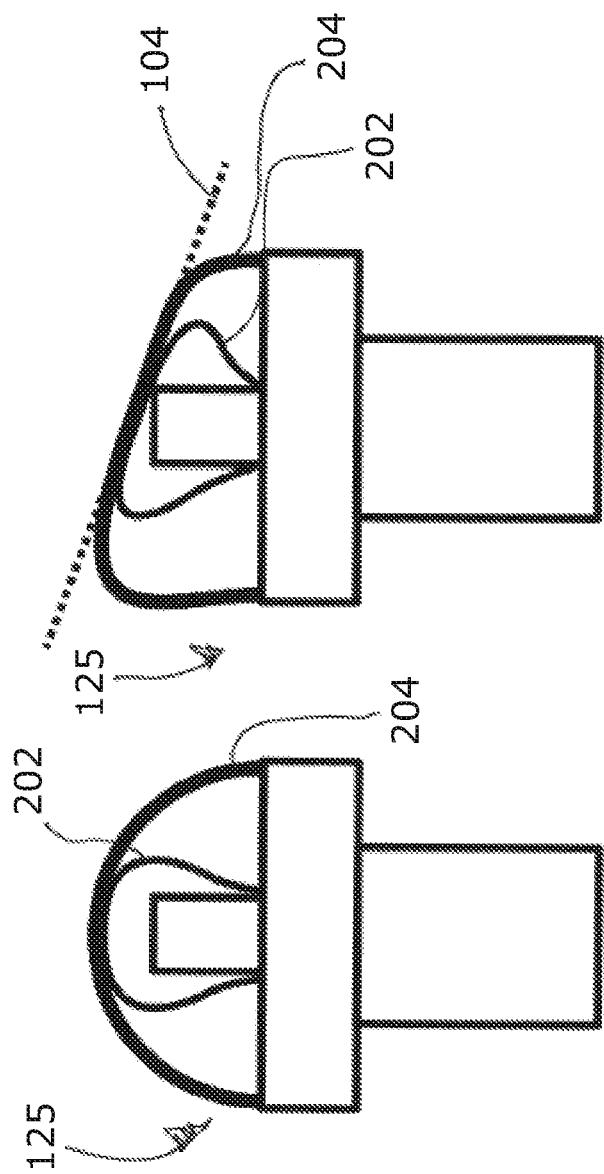

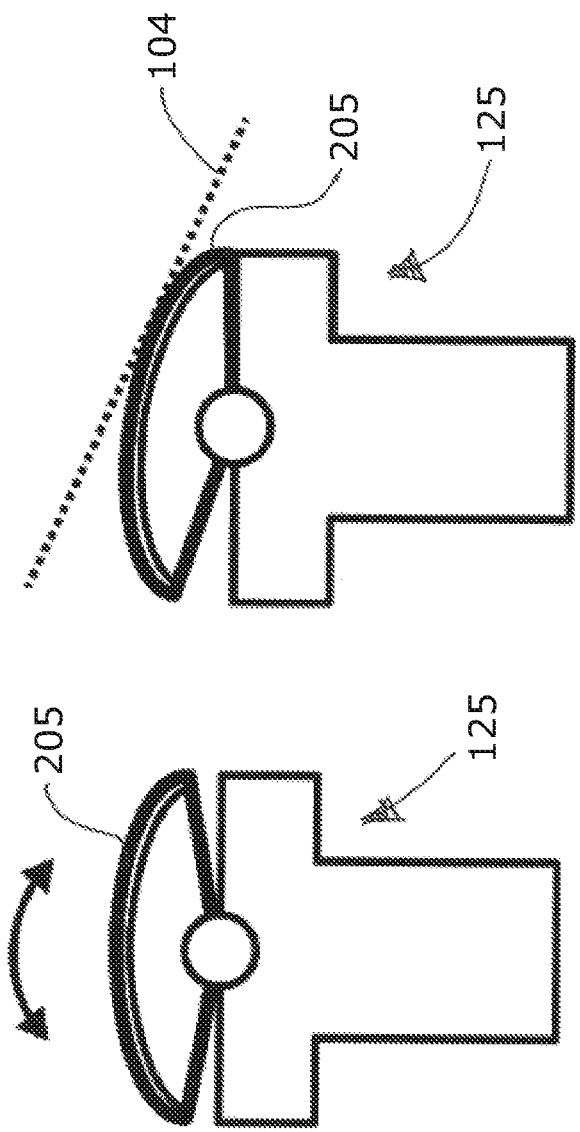

MOUTH-HELD EXTENDABLE MOUTH STYLUS FOR ACTIVATING FUNCTIONS ON A TOUCH SCREEN OR KEYS

This application is the U.S. national phase of International Application No. PCT/DK2016/050202 filed 20 Jun. 2016, which designated the U.S. and claims priority to DK Patent Application No. PA 2015 00351 filed 19 Jun. 2015, and DK Patent Application No. PA 2015 70596 filed 18 Sep. 2015, the entire contents of each of which are hereby incorporated by reference.

FIELD OF THE INVENTION

The invention relates to an extendable mouth stylus configured to be held in the mouth of the user for activating functions on a touch screen or keys.

BACKGROUND ART

The invention relates to an activation device for activating e.g. touch screens.

For disabled persons who are incapable of using their arms and/or hands, the use of touch screens is somewhat of a challenge.

Hence there is a need for an activation device allowing a person to use a touch screen without the use of his/her hands.

The present invention solves the above problem by providing an activation device for activating functions on a touch screen or keys, said activation device comprising a piston housing having a first end part and a second end part. Also, the activation device comprises a piston comprising a first rod part/piston end and a second rod part/piston end. Moreover, the activation device comprises an activation part arranged at the second rod part/piston end of the piston, characterised in that the piston rod is arranged entirely or partly inside the piston housing, and in that the piston rod is displaceably arranged in relation to the piston housing.

SUMMARY OF THE INVENTION

The present invention relates to an extendable mouth stylus for activating functions on a touch screen or keys, said extendable mouth stylus comprising:
a piston housing having a first end part and a second end part,
a piston comprising a piston rod comprising a first piston end and a second piston end,
an activation part arranged at the second piston end of the piston, and
a mouthpiece arranged at the one end of the piston housing,
  characterised in that the piston is arranged entirely or partly inside the piston housing, and in that the piston is displaceably arranged in relation to the piston housing by means of air sipped out of or puffed into the piston housing.

It is way it is achieved that a screen or keys may be activated by puffing into the piston housing.

The activation part may be named a tip, a tip part or a conductive tip.

The piston rod and the piston housing may be electrically conductive, resulting in an electrical connection being established from the first end part of the piston housing to the activation part.

In this manner a connection between the user and the touch screen is established.

In an embodiment, the activation part may comprise a magnet.

Furthermore, the first end part of the piston housing may comprise a mouthpiece arranged to be held between the upper and lower parts of the mouth of the user of the extendable mouth stylus.

The activation part may be displaceable in relation to the piston rod.

Such activation part may comprise one or more magnets.

In an embodiment, the activation part may comprise a microfibre surface.

Furthermore, the mouthpiece may comprise an aperture arranged to lead air from the mouth of the user to and/or from the piston housing.

The mouthpiece may be manufactured from a mouldable plastic material, for instance PLA.

The second end part of the piston comprising the activation part may project from the second end part of the piston housing.

The present invention also relates to an extendable mouth stylus configured to be operated with a mouth, the extendable stylus comprising:
an extending portion, i.e. the piston rod, configured to have an adjustable length, the extending portion comprising: a tube defining a longitudinal axis and an inner space, where the length of the extendable stylus is changed along the longitudinal axis, and a piston rod arranged at least partially inside the tube,
a conductive tip configured to interface with a touch screen device, wherein the conductive tip is disposed at a first end of the extending portion, and
a mouthpiece configured to engage the mouth of a user, wherein the mouthpiece is disposed at a second end of the extending portion, opposite the first end, wherein the mouthpiece comprises an aperture to allow communication of air from the mouthpiece to the inner space of the tube.

In this way it is possible for the user by sipping and puffing to adjust the length of the extending portion, i.e. extending by puffing and shortening by sipping.

The extendable mouth stylus may further comprise a control mechanism disposed proximate the second end of the extending portion, wherein the control mechanism is configured to control the length of the extending portion, i.e. the piston rod. The control may be based on changing direction of airflow by the user.

The extendable mouth stylus may comprise a slidable weight arranged to slide on the piston rod. In this way it is achieved that when the piston rod is moved in either the one or the other direction, the slidable weight will, upon stop of the movement of the piston rod, slide towards a stop, and in this way prevent the piston rod from bouncing. Bouncing may cause the mouth stylus to "double tap" on the screen when pushed away from the user. When the piston rod is moved towards the user, the slidable weight will ensure a better comfort for the user due to less bouncing which may be felt in the mouth of the user.

Moreover, the piston rod may be made from a conductive material, e.g. graphite or metal. The piston rod may be made from a composite material comprising a composite rendering the piston rod electrically conductive.

Further, the mouthpiece may comprise a path arranged to provide flow of air from the mouth of the user to the piston housing. In this way the air sipped or puffed by the mouth of the user can be used to apply a force to the piston and thereby move the piston rod.

Also, the mouthpiece may be made from an FDA-recognised material unharmful to the user.

Furthermore, this piston may be of a conductive material.

The tip may be conductive. The tip may be made from a conductive cloth. The tip may be retractable into a tip cover. The tip may be made of a conductive basket-shaped conductive material.

Moreover, the parts of the mouth stylus may be kept in position by glue.

Further, the mouthpiece may comprise wings which during use are arranged between the upper and lower parts of the user's mouth, whereby the user can hold the mouth stylus.

The mouthpiece may be arranged at an angle in relation to the longitudinal axis of the mouth stylus. In this way it is achieved that the user gains a better angle in relation to the appliance to be activated by use of the mouth stylus. The angle may be 2°-40°, or 4°-30°, or more preferred 6°-20°, or most preferred 8°-10°.

The mouthpiece may be electrically conductive. The mouthpiece may comprise an electrically conductive material to enable electrical conductivity from the user to the piston housing.

Also, the mouthpiece may be made from a conductive material.

Furthermore, the mouthpiece may be integrated with the piston housing.

The mouthpiece may comprise an aperture arranged to establish contact between the lips of the user and the piston housing. In this way an electrically conductive path is created from the user to the piston housing and hence to the tip of the mouth stylus.

The piston housing may comprise an air aperture, i.e. an air intake/air outlet.

In this way excessive air from the user puffed into the mouthpiece and further into the piston housing has a path along which it may escape from the piston housing. Similarly, when sipping and hence drawing the piston towards the user, an easy path of air to push the piston is achieved.

Moreover, the air aperture may be arranged at a position in the piston housing further away from the user than the piston itself. In this way it is achieved that the flow path of the air initiated by the user from the air aperture to the mouthpiece always passes the piston and hence moves the piston and piston rod. In this way the overall length of the mouth stylus is extended when air is puffed into the mouth stylus and shortened when air is sipped by the user.

BRIEF DESCRIPTION OF THE DRAWINGS

FIG. 10 shows a damping mechanism in a second position, FIGS. 11A and 11B show another embodiment of a damping mechanism, FIGS. 12A and 12B show yet another embodiment of a damping mechanism, FIGS. 13A and 13B show embodiments of the tip, FIGS. 14A and 14B show yet further embodiments of the tip, FIGS. 15A and 15B show even further embodiments of the tip.

DETAILED DESCRIPTION OF THE INVENTION

Figure 1:
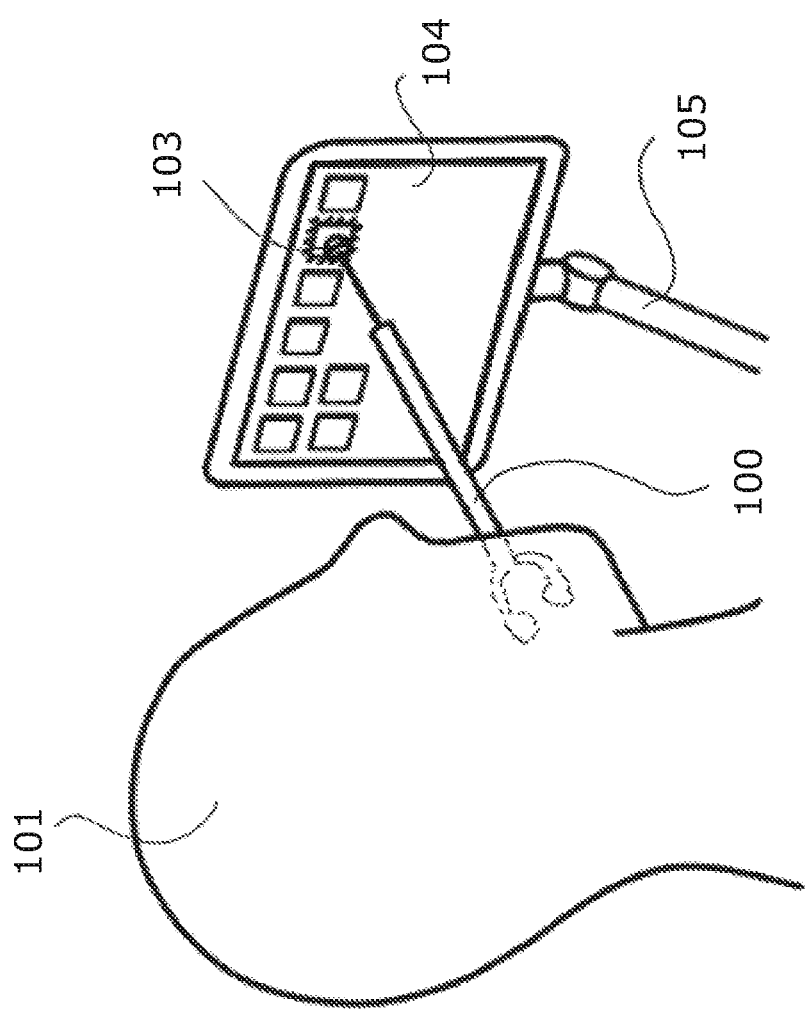
FIG. 1 shows a user using the mouth stylus according to the present invention.

FIG. 1 shows an extendable mouth stylus 100 held in the mouth of a user 101. The extendable mouth stylus 100 comprises an activation part 103 shown in a projected position in contact with a touch screen 104. The touch screen 104 is held by an arm or a rack 105.

Figure 2:
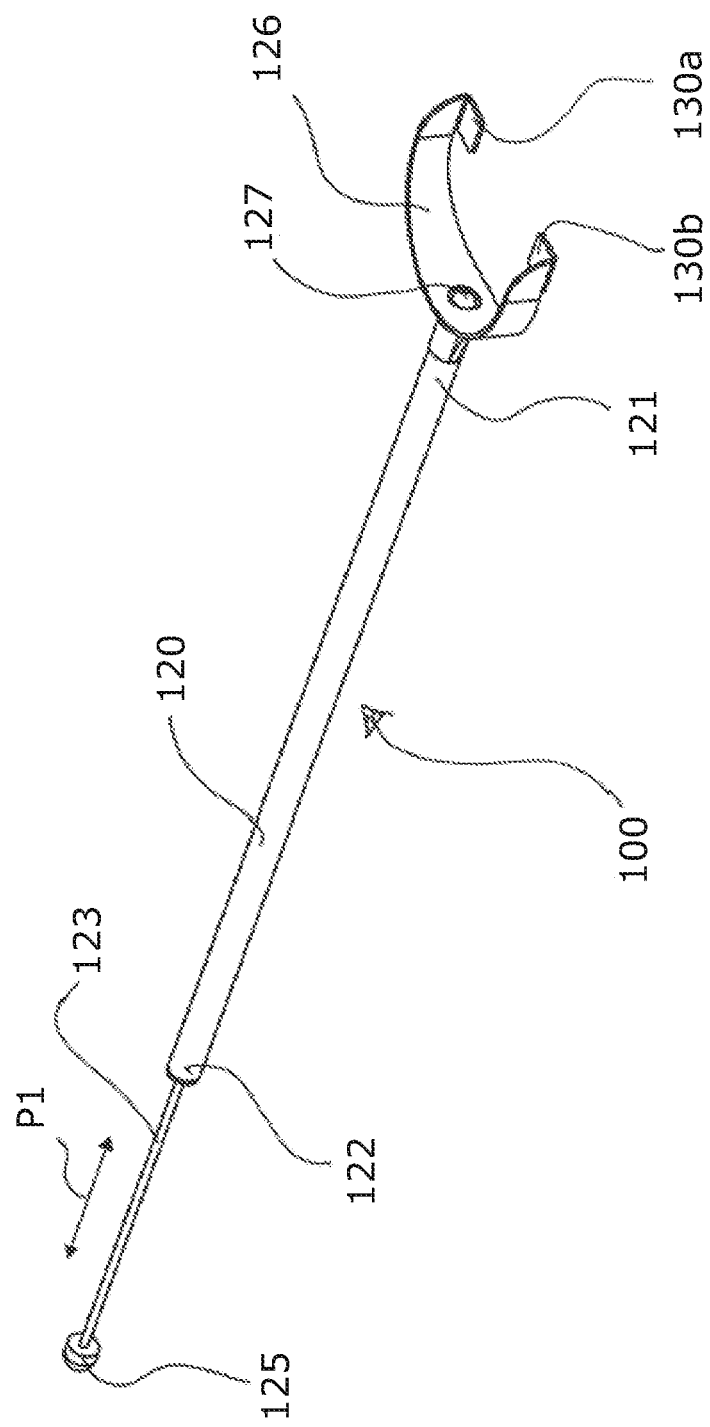
FIG. 2 shows an embodiment of the mouth stylus according to the present invention.

FIG. 2 is a perspective view of the extendable mouth stylus 100 comprising a piston housing 120 and a piston rod 123 which is displaceable in the longitudinal direction of the piston housing 120. The longitudinal direction of the piston housing 120 and the longitudinal direction of the extendable mouth stylus coincide. The piston housing comprises a first end part 121 and a second end part 122. The piston 123 is shown with the piston 123 extending outward from the second end part 122 of the piston housing 120. The piston comprises an activation part 125 arranged to establish electrical contact between e.g. a touch screen (not shown), the piston 123, the piston housing 120 and a mouthpiece 126. As shown in FIG. 1, the mouthpiece 126 will typically be held by the user 101 in his/her mouth. The mouthpiece comprises an aperture 127, through which the user may sip or puff air and hence control the movement of the piston 123.

The piston 123 is thus displaceably arranged in the piston housing 120. The displacement occurs along the longitudinal axis of the piston housing 120 indicated by the arrow P1. The mouthpiece 126 comprises biting areas 130a and 130b arranged in order to allow the user to bite his/her teeth together around these biting areas and thereby hold the mouthpiece 126 and the entire extendable mouth stylus 100 in a given position in relation to the head of the user.

Figure 3:
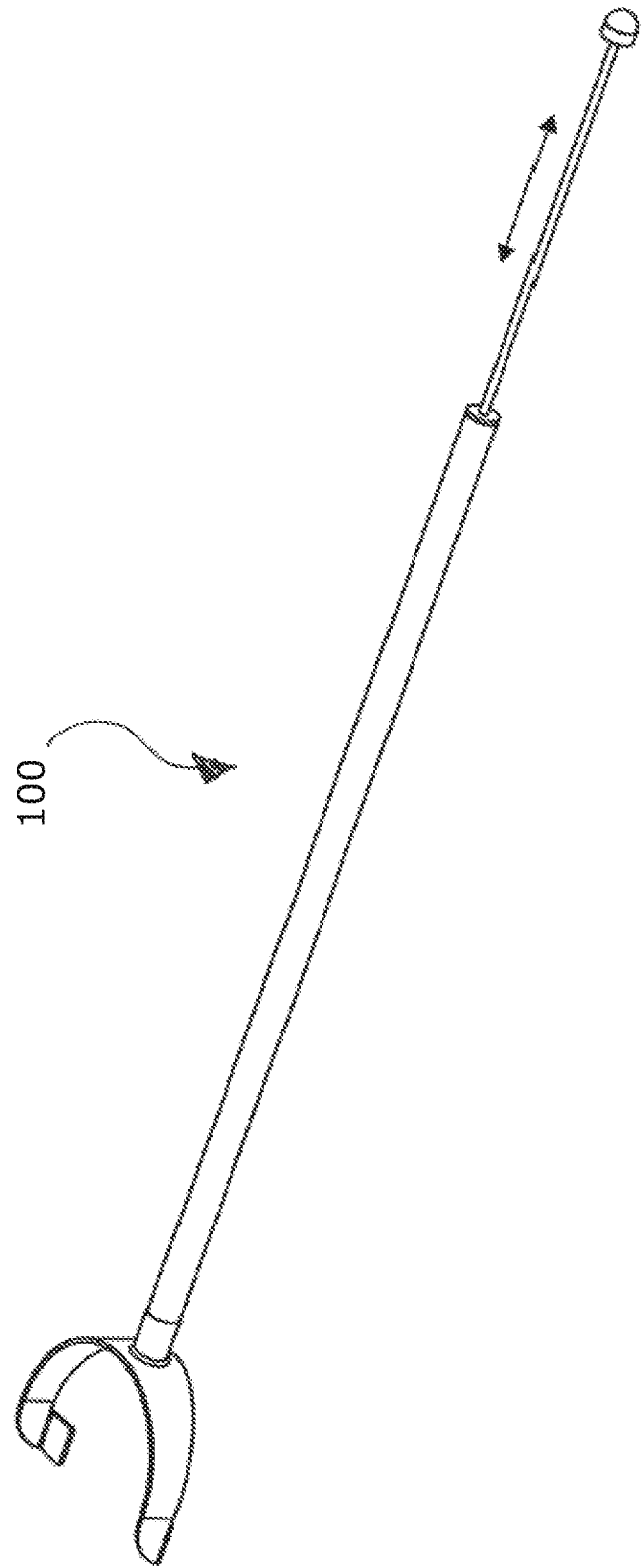
FIG. 3 shows an embodiment of the mouth stylus according to the present invention.

Similarly to FIG. 2, FIG. 3 shows a perspective view of the extendable mouth stylus 100.

Figure 4:
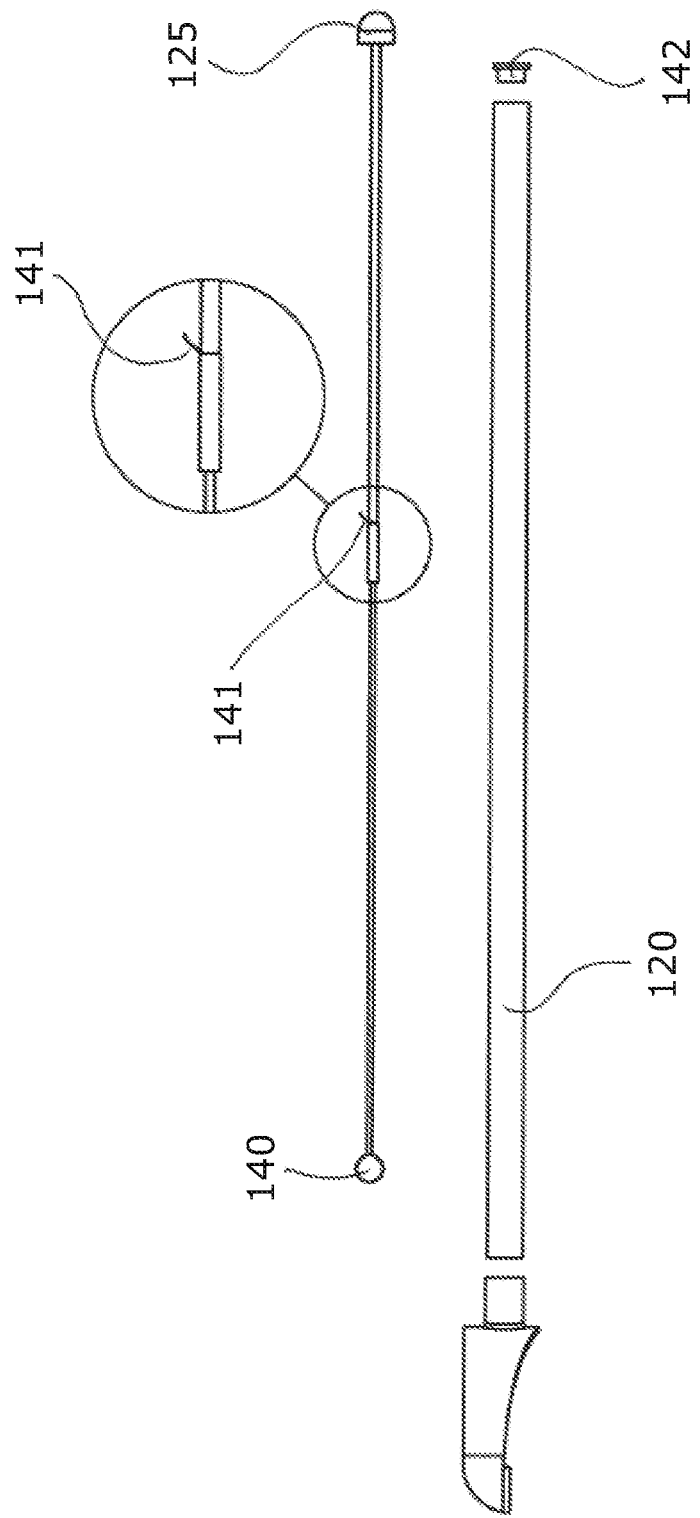
FIG. 4 shows the parts of a conductive mouth stylus according to the present invention.

FIG. 4 shows an embodiment of the extendable mouth stylus 100, wherein the piston rod/the piston 123 has been taken out of the piston housing 120. In the first piston end of the piston rod, the piston head 140 itself is shown. The piston head 140 has been adapted to the inner diameter of the piston housing 120 so that the piston head 140 may be easily displaced without a large amount of air passing by the piston head. Thereby it is obtained that the displacement of the piston rod 123 (shown in FIG. 2) responds to even the smallest conceivable air impact caused by the user. It is possible to adjust the response by adjusting the clearance around the piston 140. The piston rod comprises an activation part 125 and an electrically conductive part 141 ensuring a constant electrical connection between the piston rod 123 (shown in FIG. 2) and the piston housing 140. The electrical connection is necessary in relation to the activation of touch screens. The electrical connection is necessary in relation to the activation of touch screens. The electrical connection is not necessary if the extendable mouth stylus is used to activate mechanical buttons or contacts, e.g. a traditional keyboard or a light switch. In the shown embodiment, the piston housing comprises a bushing 142, resulting in the provision of precise guidance of the piston rod 123 (shown in FIG. 2).

Figure 5:
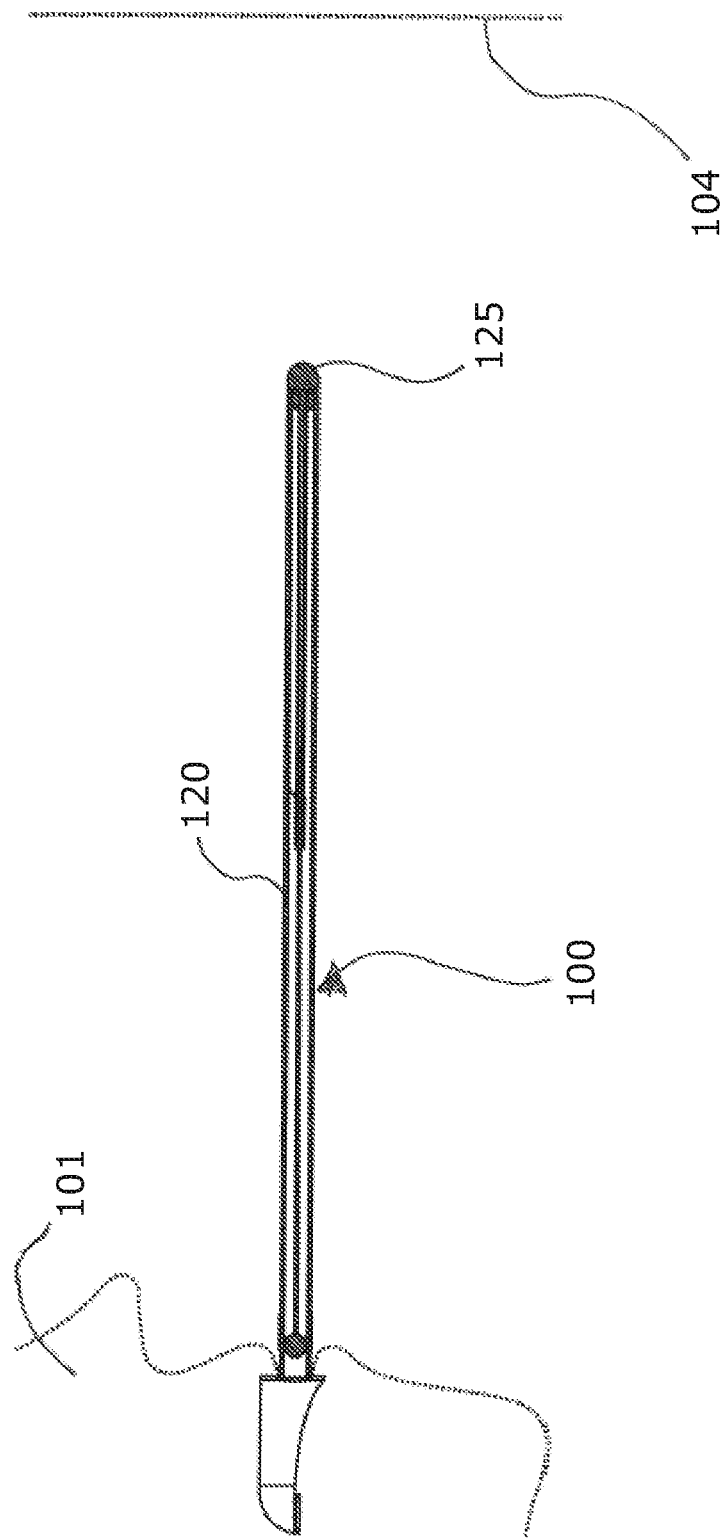
FIG. 5 shows the mouth stylus arranged in the mouth of a user in retracted position.

FIG. 5 shows a sectional view of the extendable mouth stylus 100 held in the mouth of a user 101. In this view, the piston 123 (shown in FIG. 2) is shown in a retracted position and the activation part 125 is in contact with the piston housing 120. The piston rod 123 may be longer, so that the activation part, in a fully retracted position of the piston rod 123 (shown in FIG. 2), will not be in contact with the piston housing. The extendable mouth stylus is thus shown in a state in which it is not in contact with the touch screen 104 (shown schematically by a dotted line).

Figure 6:
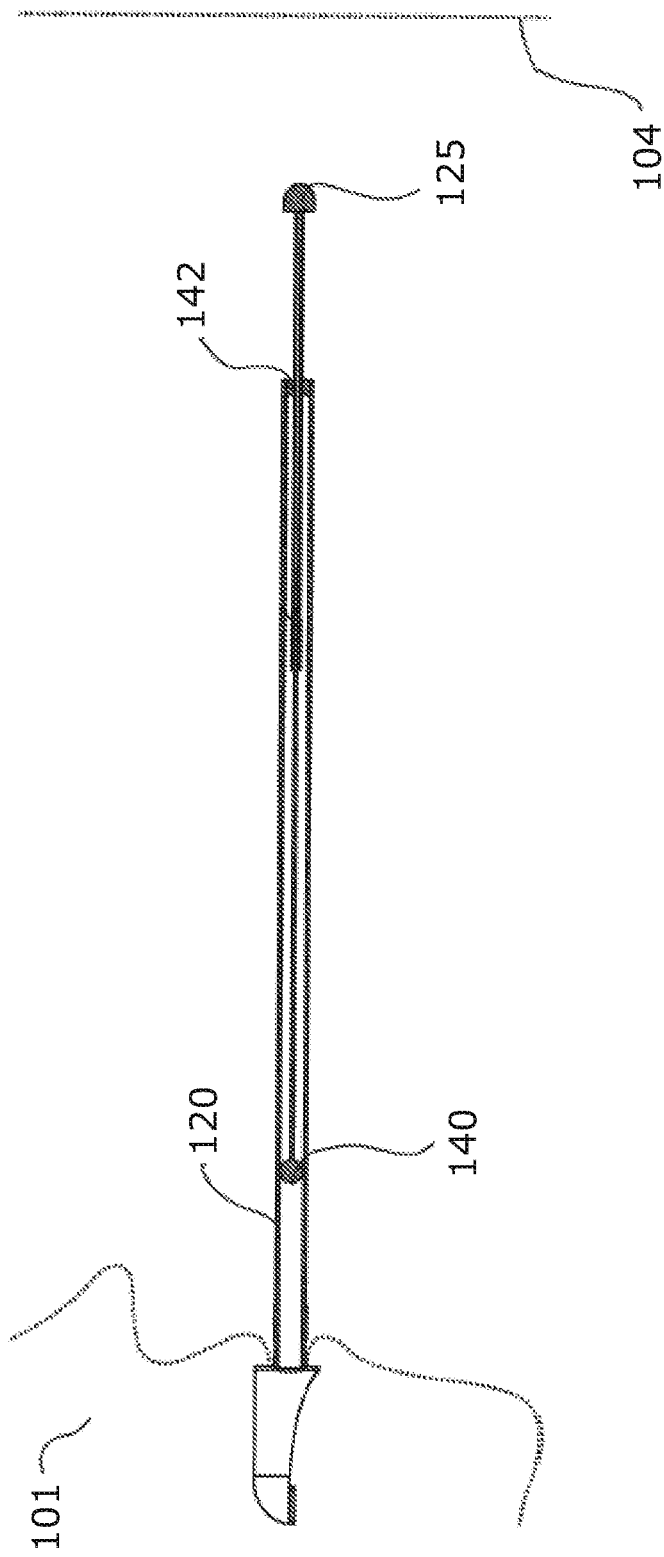
FIG. 6 shows the mouth stylus arranged in the mouth of a user in extended position.

FIG. 6 shows that the user 101 has puffed lightly into the extendable mouth stylus (via the aperture 127, not shown), and the piston 140 has thus been affected by a force, and the entire piston rod 123 (shown in FIG. 2) has been projected in part out from the piston housing 120. It is seen that the bushing 142 holds the piston rod 123 radially in the middle of the cross section of the piston housing 120. The activation part 125 is not yet in contact with the touch screen 104.

Figure 7:
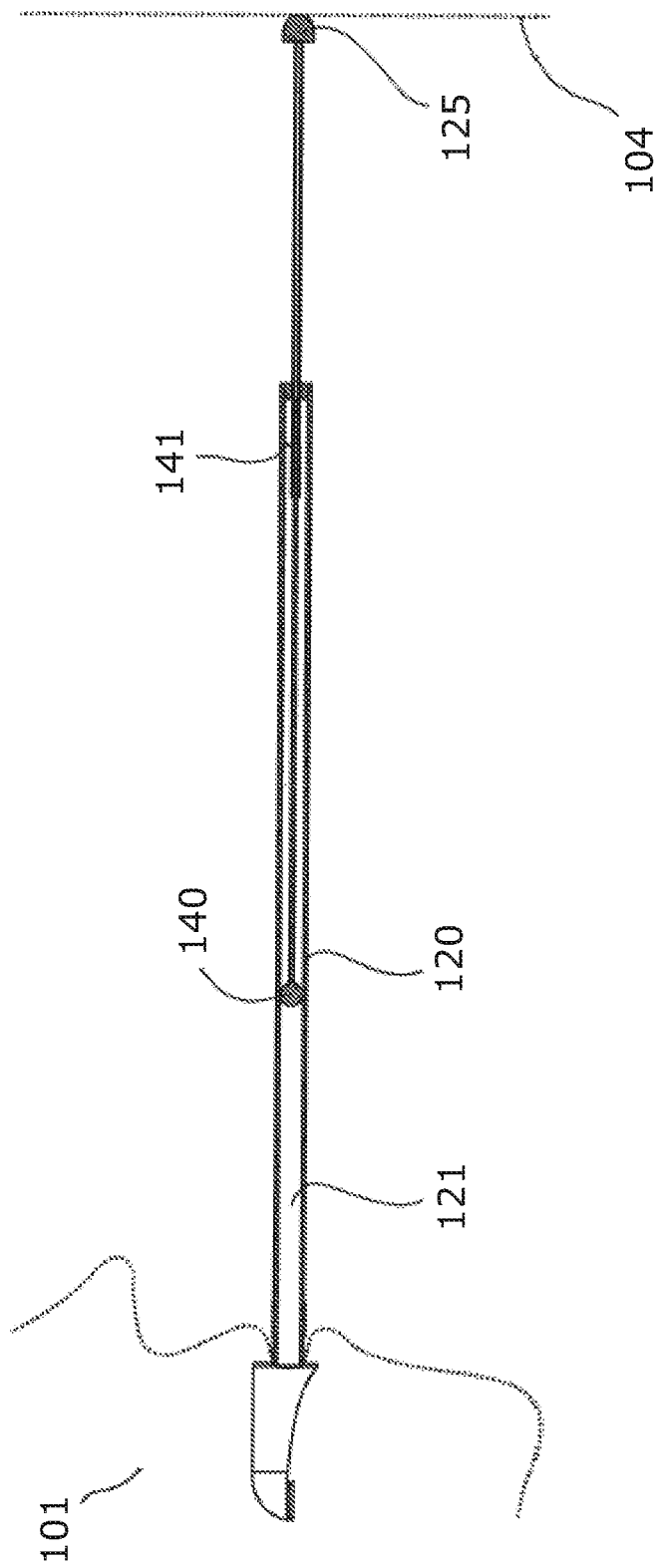
FIG. 7 shows the mouth stylus arranged in the mouth of a user in an extended position in which the tip is in contact with a screen, e.g. a touch screen.

FIG. 7 shows that the user has puffed with a sufficient force into the piston housing 120 (via the aperture 127 of the mouthpiece 126 not shown) causing the excess pressure created in the first end part 121 of the piston housing to project the piston 140 and thus the piston rod 123 (shown in FIG. 2) with the activation part 125 all the way up to the touch screen 104. Since there is an electrical connection from the user's mouth via the mouthpiece 126 (shown in FIG. 2) to the piston housing 120 and further on via the conductor 141 to the activation part 125, it is possible to activate e.g. icons on the touch screen.

Figure 8:
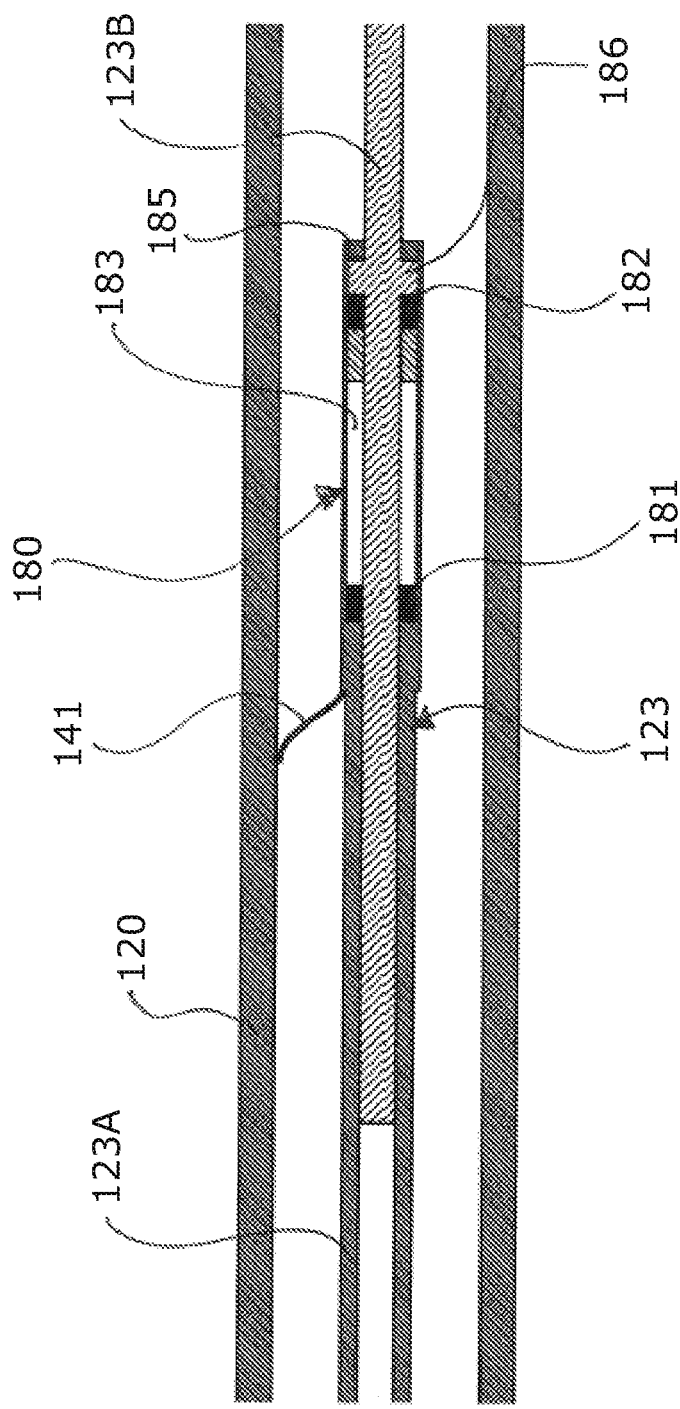
FIG. 8 shows a damping mechanism in a first position.

FIG. 8 shows an enlarged sectional view of the area of the piston housing 120 in which the electrical conductor 141 is mounted. The electrical conductor may be arranged in other locations in which connection between the piston rod 123 and the piston housing 120 is established. Similarly, this sectional view shows that the piston rod comprises a springy mechanism 180. The springy mechanism 180 is arranged to absorb small mechanical shocks in connection with the activation part 123 touching e.g. the touch screen 104 (not shown). The springy mechanism 180 reduces the risk of double taps on the screen. Without the springy mechanism, the activation part would possibly bounce on the screen and hence introduce undesired double tapping. In this embodiment, the springy mechanism 180 is constituted by two magnets 181 and 182 arranged in a tubular spring area 183, in which the magnets 181 and 182 counteract each other in such a way that they repel each other. The piston rod is thus divided into two parts, a first rod part 123A and another rod part 123B. In combination, the two rod parts are denoted "123". The spring area may also be open. Hence, the magnets 181 and 182 affect each other, and since the first magnet 181 is retained in the first rod part 123A, and the second magnet 182 is retained in the second rod part 123B, the two rod parts 123A and 123B are pushed away from each other. A stop 185 mounted at the end of the first rod part 123A cooperates with a projection 186 on the second rod part 123B, whereby the second rod part 123B cannot be displaced out of the first rod part 123A.

Figure 9:
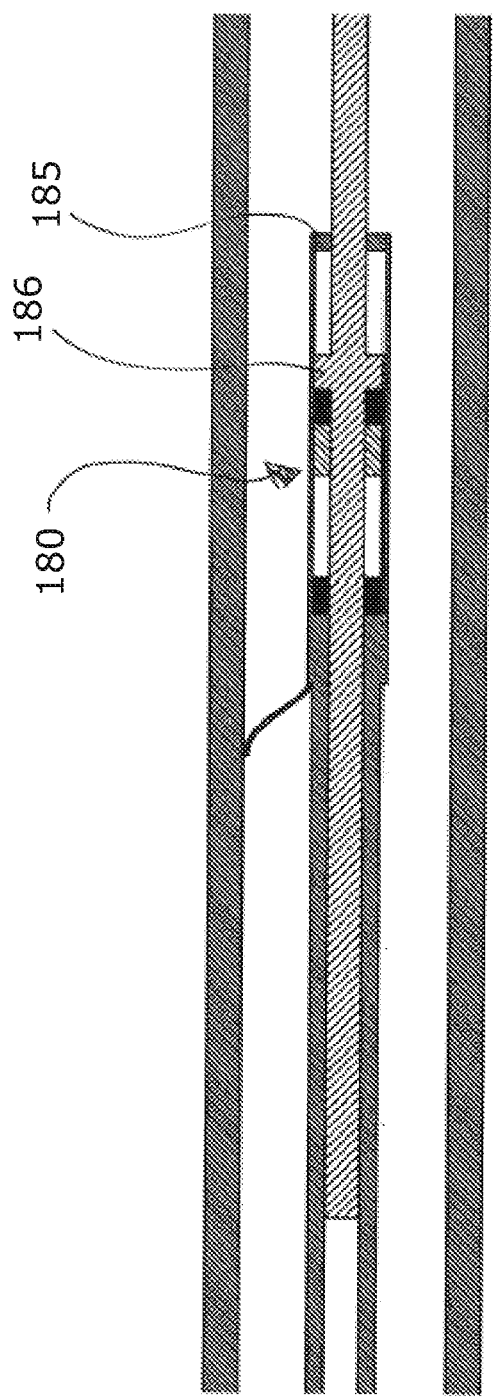
FIG. 9 shows a damping mechanism in an intermediate position.

Similarly to FIG. 8, FIG. 9 shows a sectional view of the springy mechanism 180 shown in a centre position, i.e. in a position in which there is slight contact between an item and the activation part 125 (not shown). It is seen that the stop 185 and the projection 186 are no longer in contact.

Similarly to FIGS. 8 and 9, FIG. 10 shows a sectional view of the springy mechanism 180, wherein the second rod part 123B is pushed to the furthest degree possible into the first rod part 123A.

FIGS. 11A and 11B show another embodiment of a springy mechanism 180, wherein the springy part comprises a pliant part 190. The pliant part may e.g. be made of rubber or a foamed material. FIG. 11A shows the second rod part 123B displaced almost to its maximum out from the first rod part 123A. FIG. 11B shows the second rod part pushed part of the way into the first rod part 123A.

FIGS. 12a and 12B show another embodiment of a springy mechanism 180, wherein a spring 192 is used between the first rod part 123A and the second rod part 123B.

FIGS. 13A and 13B show an embodiment of the activation part 125. The activation part 125 comprises a band 200 which is electrically conductive. The band may be made of nylon with copper or silver or similar conductive metal woven into it. The band 200 could also be made of silk or cotton. The band 200 ensures that electrical contact to the touch screen 104 is created in a way that is slightly pliant. In this way it is achieved that unnecesary resistance in connection with a "swipe" when the activation part 125 is drawn across the screen 104 is eliminated. Similarly it is obtained that the activation part 125 does not bounce on the screen. FIG. 13B shows how the band 200 gives in.

FIGS. 14A and 14B show an embodiment of the activation part 125, wherein a conductor 202 is covered by a conductive, protective material 204.

FIGS. 15A and 15B show an embodiment of an activation part 125 comprising a tiltably arranged contact part 205. Hence, the tiltably arranged contact part 205 provides a pliant effect when the screen 104 is touched.

The activation is effected by the creation of a positive pressure in the first end part 121 of the piston housing driving the piston 140, the piston rod 123 and the activation part 125 forward towards a touch screen or a button. The process is reversed by creating a negative pressure in the first end part 121 of the piston housing. This principle is illustrated in FIGS. 5-7.

The contact face of the activation part 125 consists of e.g. an electrically conductive microfibre. In an embodiment, the mouthpiece 126 may be electrically conductive. In this way electrical connection is established from the mouthpiece 126 via the piston housing 120 and the piston rod 123 to the activation part 125. In an embodiment, the activation part 125 may be pliant in relation to the piston rod 123.

In order to ensure that the activation part retains contact with a screen or a button during the course of the entire activation, the piston rod is provided with a shock absorber/a springy mechanism 180. The shock absorber/the springy mechanism 180 absorbs the impulse from the force created when the activation part 125 touches a face. This is effected by the piston rod 123 comprising two parts 123A and 123B which are kept apart by two opposite magnets (181, 182). One is mounted on the first part 123A of the piston rod, and the other is connected with the second part 123B of the rod.

The strength of the magnets is only just sufficient for holding the rod parts 123A, 123B apart during acceleration of the piston. The pressure in the piston housing may be applied by the user by means of his/her mouth. A mouthpiece 126 may therefore be mounted on the first end of the piston housing. The mouthpiece may be shaped according to the mouth of the user 101. All parts are connected in order to establish an electrical connection between the mouthpiece and the activation part.

Figure 16:
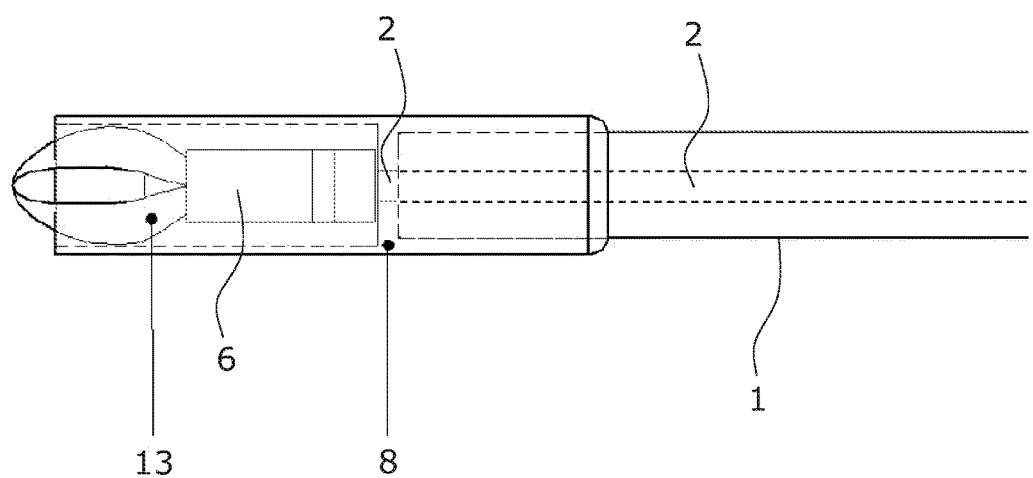
FIG. 16 shows a conductive cloth tip retracted.

FIG. 16 shows a further embodiment of the invention. The activation device is an extendable stylus configured to interface with a touch screen device. The extendable stylus comprises a tip 13 and a tip cover 8. In the shown embodiment, the tip 13 is a conductive piece of cloth, but may be made from various materials. In this embodiment, when the tip 13, i.e. cloth, is retracted into the tip cover 8, the cloth is straightened and hence re-shaped to its initial shape after having touched a screen or similar.

Figure 17A:
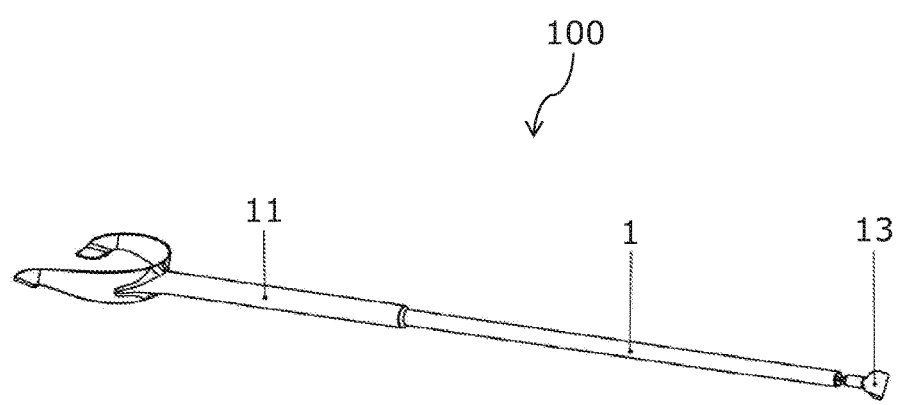
FIGS. 17A and 17B show embodiments of the mouth stylus having a cloth tip.
Figure 17B:
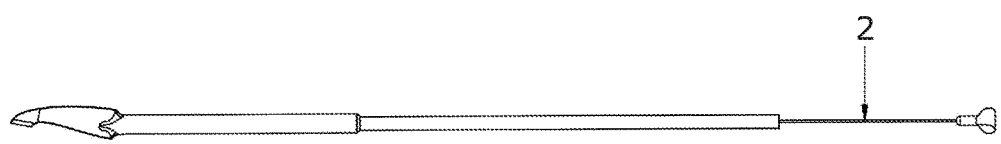

FIG. 17A and FIG. 17B show an embodiment of the extendable mouth stylus. In this embodiment, the extendable mouth stylus comprises a piston housing 11 and a piston housing extension 1. It is seen that the tip 13 is pushed slightly out of the piston housing extension 1 (the tip housing not shown, see FIG. 16). In FIG. 17B it is seen that the piston is pushed further out of the piston housing extension 1 and more of the piston rod 2 is visible.

Figure 18:
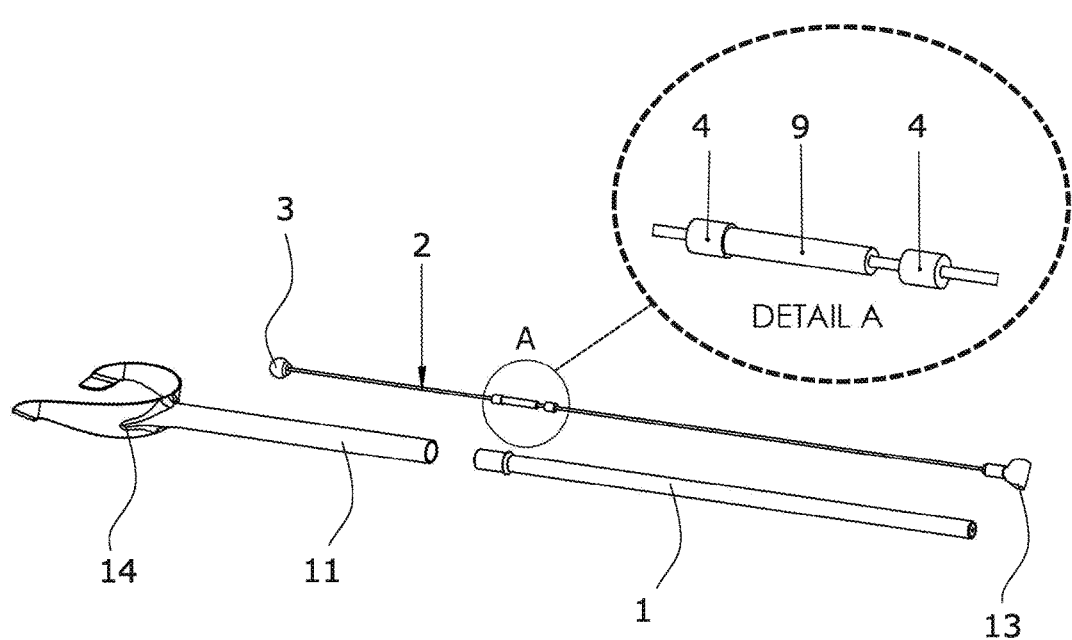
FIG. 18 shows an embodiment having a hammer.

FIG. 18 shows a partly exploded view of the mouth stylus of FIG. 17. It is seen that the mouth stylus comprises a piston housing 11 and a piston housing extension 1 and a mouthpiece 14. The piston rod 2 is substantially arranged inside the piston housing 11 and the housing extension 1. The piston 3 and the tip 13 are positioned in each end of the piston rod 2. Along the piston rod 2, a hammer 9 or inertia mechanism is arranged. The inertia mechanism comprises a hammer 9 and two stops 4. The stops 4 are attached to the piston rod 2, and the hammer is slidably arranged on the piston rod 2. Hence, the hammer 9 is capable of moving from the one stop to the other. In this embodiment, the hammer 9 is tubular and the hammer 9 is arranged by having the piston rod extending through the inner aperture of the tube, i.e. the inner aperture of the hammer 9.

Figure 19A:
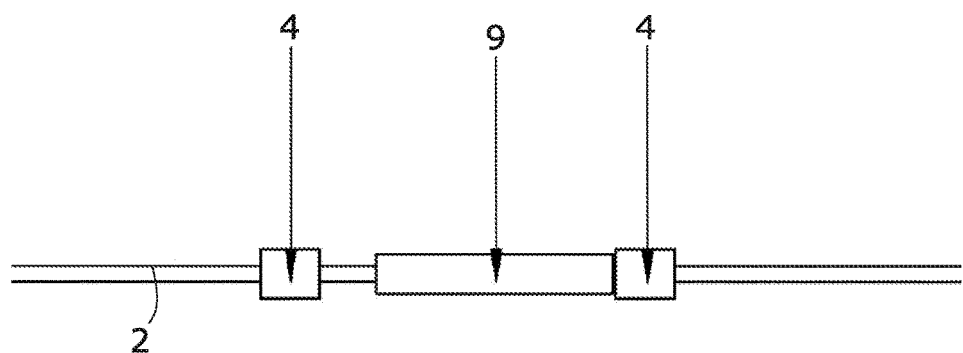
FIGS. 19A and 19B show detailed views of the hammer.
Figure 19B:
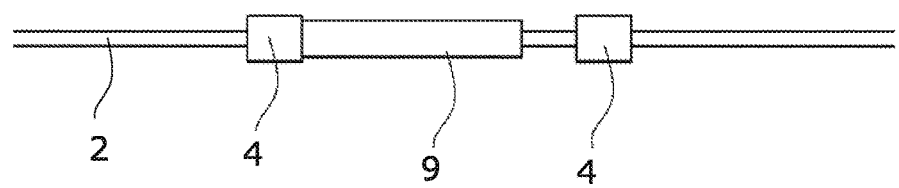

FIGS. 19A and 19B show that the hammer 9 can move from the one stop to the other stop 4. When the piston is stopped, the hammer 9 continues to travel until the hammer 9 meets a stop 4. When the hammer meets a stop 4, the kinetic energy from the hammer will be transferred to the piston rod 2 and hence apply an additional force to the tip of the mouth stylus. In this way it is achieved that the tip does not "double tap", e.g. when writing text on a touch screen.

Figure 20:
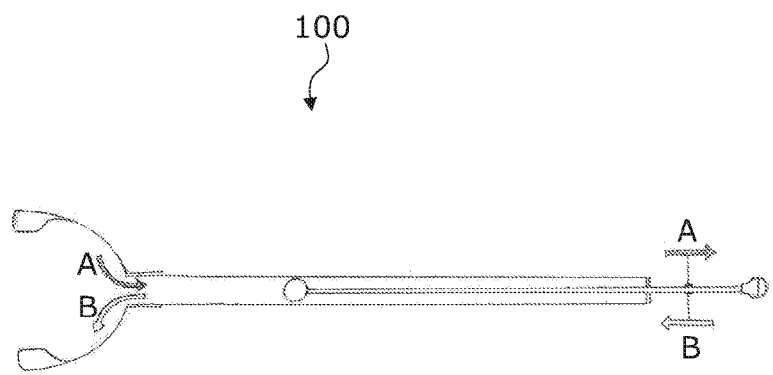
FIG. 20 shows a schematic drawing of the air flow in the mouth stylus.

FIG. 20 shows a cut-through of a sketched stylus. The sketch shows, in a simple manner, how the general concept of the mouth stylus 100 is applied. It seen that when the user puffs air through the mouthpiece, the air forces the piston in direction of arrow A. When the user sips, the piston is moved in direction B.

Figure 21:
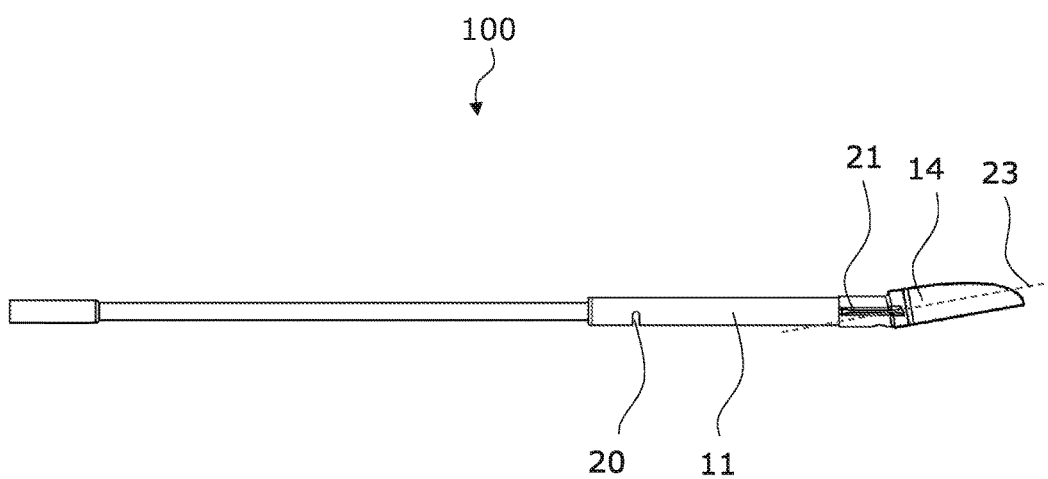
FIG. 21 shows partly the flow path.

FIG. 21 shows an embodiment of the mouth stylus where the piston housing 11 comprises an air aperture 20, i.e. an air intake and an air outlet. The mouthpiece 14 comprise a path 21 for allowing communication of air through the mouthpiece to the piston housing 11. The mouthpiece 14 is shown to be tilted 10° in relation to the longitudinal axis of the piston housing 11 and/or the piston housing extension.

Figure 22:
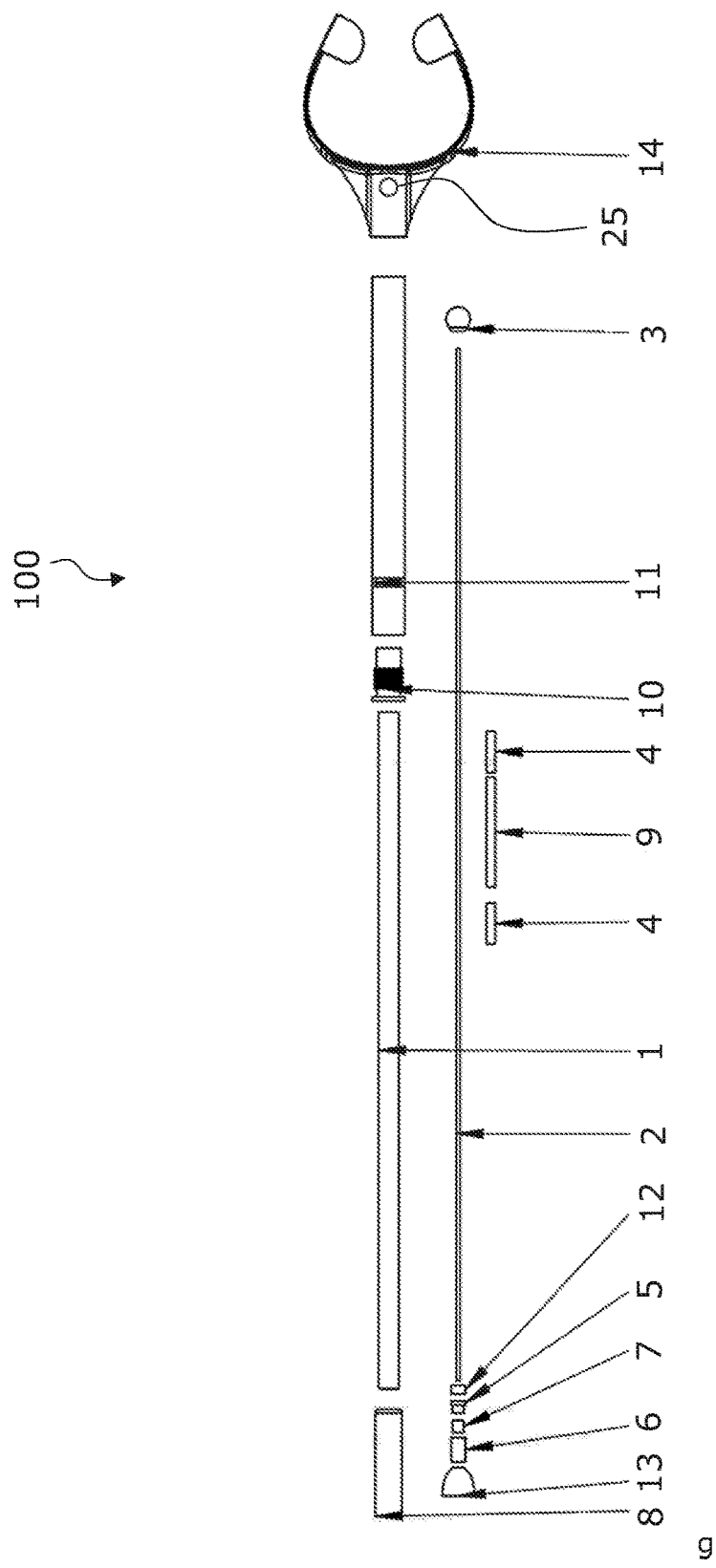
FIG. 22 shows the detailed parts of the mouth stylus.

FIG. 22 shows the parts of an embodiment of the mouth stylus 10. The extendable mouth stylus 100 comprises a piston extension housing 1, a piston rod 2 having a piston 3 arranged at the one end and a tip 13 at the other end. The tip 13 is affixed to the piston housing by a number of parts 5, 6, 7, 12 for entrapping the ends of the cloth of the tip 13. Entrapping the ends of the conductive piece of cloth (not shown) is carried out by forcing each end of the cloth inside a tubular part such that the cloth is positioned between the tubular part and further parts arranged at the rims of the tubular parts. In this way the cloth is fixated to the tubular part. The tubular part 6 is affixed to the piston rod e.g. by glue or a press fit. The mouth stylus comprises a damper 12 in form of a silicone ring. The damper 12 ensures that by stopping the piston upon sipping, the user does not feel a bump or stroke to his or her teeth/mouth. The damper 12 ensures that the user may use the mouth stylus for a long period without fatigue. The hammer 9 and the stops 4 are already described above. The extension piston housing 1 and the piston housing 11 are affixed to each other via the fitting 10. The fitting 10 may connect the two housings by glue, a press fit, threads or similar. It is furthermore seen that the mouthpiece comprises an aperture 25. This aperture provides electrical contact between the mouth of the user and the mouth stylus, in particular the piston 3 and piston rod 2, and since the piston 3 and the piston rod 1 are conductive, the user is electrically in contact with the tip 13. In this way it is achieved that both electrically responsive touch screens as well as pressure sensitive touch screens can be activated using the mouth stylus according to the present invention.

Although the invention has been described in the above in connection with preferred embodiments of the invention, it will be evident for a person skilled in the art that several modifications are conceivable without departing from the invention as defined by the following claims.

The invention claimed is:

1. An extendable mouth stylus for activating functions on a touch screen or keys, said extendable mouth stylus comprising:
   a piston housing having a first end part and a second end part,
   a piston comprising a piston rod comprising a first piston end and a second piston end,
   an activation part arranged at the second piston end of the piston rod, and
   a mouthpiece arranged at the first end part of the piston housing, the mouthpiece having a mouthpiece aperture,
   wherein the piston rod is arranged entirely or partly inside the piston housing, and wherein the piston and piston rod are displaceably arranged in relation to the piston housing by means of air sipped out of or puffed into the piston housing via the mouthpiece aperture, and
   wherein the piston housing comprises an air aperture separate from the mouth aperture, the air aperture acting as an air intake or outlet as the piston rod and piston are reciprocated in the piston housing.

2. An extendable mouth stylus according to claim 1, wherein the piston rod and the piston housing are electrically conductive, resulting in an electrical connection being established from the first end part of the piston housing to the activation part.

3. An extendable mouth stylus according to claim 1, wherein the activation part comprises a magnet.

4. An extendable mouth stylus according to claim 1, wherein the mouthpiece is arranged to be held between the upper and lower parts of the mouth of a user of the extendable mouth stylus.

5. An extendable mouth stylus according to claim 4, wherein the mouthpiece is manufactured from a mouldable plastic material.

6. An extendable mouth stylus according to claim 1, wherein the activation part is displaceable in relation to the piston rod.

7. An extendable mouth stylus according to claim 1, wherein the activation part comprises one or more magnets.

8. An extendable mouth stylus according to claim 1, wherein the activation part comprises a microfibre surface.

9. An extendable mouth stylus according to claim 1, wherein the mouth aperture is arranged to lead air from the mouth of a user to and/or from the piston housing.

10. An extendable mouth stylus according to claim 1, wherein the activation part projects from the second end part of the piston housing.

11. An extendable mouth stylus according to claim 1, wherein the mouthpiece is made from a conductive material.

12. An extendable mouth stylus according to claim 1, wherein, the mouthpiece is integrated with the piston housing.

13. An extendable mouth stylus according to claim 1, wherein the aperture is arranged to establish pneumatic communication between the lips of the user and the piston housing.

14. An extendable mouth stylus according to claim 1, wherein the air aperture housing extends from an exterior of the piston to the inside of the piston housing,
  the air aperture being located at the second end part of the piston housing, and
  wherein the piston is positioned between the mouth aperture and the air aperture as the piston and piston rod are reciprocated in the piston housing.

15. An extendable mouth stylus according to claim 14, wherein the air aperture acts as an intake when the piston moves towards the mouthpiece aperture, and the air aperture acts as an outlet when the piston moves towards the air aperture.

16. An extendable mouth stylus according to claim 1, further comprising an inertia mechanism configured to help reduce the chance of the activation part "double-tapping" the touch screen or keys.

17. An extendable mouth stylus configured to be operated with a user's mouth, the extendable stylus comprising:
  an extending portion configured to have an adjustable length, the extending portion comprising: a tube defining a longitudinal axis and an inner space, where a length of the extendable mouth stylus is changed along the longitudinal axis, and a piston rod arranged at least partially inside the tube,
  a conductive tip configured to interface with a touch screen device, wherein the conductive tip is disposed at a first end of the extending portion,
  a mouthpiece configured to engage the mouth of a user, wherein the mouthpiece is disposed at a second end of the extending portion, opposite the first end, wherein the mouthpiece comprises an aperture to allow communication of air from the mouthpiece to an inner space of the tube, and
  an inertia mechanism arranged along the piston rod, the inertia mechanism being configured to translate together with the piston rod when the piston rod is moving, and the inertia mechanism is configured to continue travel along the piston rod for a distance when the piston rod is stopped.

18. An extendable mouth stylus according to claim 17, wherein the inertia mechanism comprises a pair of stops mounted on a piston rod and a hammer positioned between the two stops, the hammer being movable along the piston rod between the two stops when the piston rod is stopped.

19. An extendable mouth stylus according to claim 17, further comprising an air aperture provided on the piston housing, separate from the mouth aperture, the mouth aperture and the air aperture being positioned at opposite ends of the tube.

* * * * *